(12) United States Patent
Schwarz et al.

(10) Patent No.: US 7,622,558 B2
(45) Date of Patent: Nov. 24, 2009

(54) ANTIBODIES WHICH ARE DIRECTED AGAINST THE MARBURG I POLYMORPHISM OF FACTOR VII-ACTIVATING PROTEASE (FSAP), AND THEIR PREPARATION AND USE

(75) Inventors: Herbert Schwarz, Lohra (DE); Harald Althaus, Wetter (DE); Bodo Fischer, Marburg (DE); Thomas Wissel, Lahntal-Sarnau (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 98 days.

(21) Appl. No.: 11/208,881

(22) Filed: Aug. 23, 2005

(65) Prior Publication Data

US 2006/0045879 A1 Mar. 2, 2006

(30) Foreign Application Priority Data

Aug. 24, 2004 (DE) ....................... 10 2004 041 104
Jun. 6, 2005 (DE) ....................... 10 2005 026 163

(51) Int. Cl.
*C07K 16/00* (2006.01)

(52) U.S. Cl. ............ 530/387.9; 530/388.1; 530/388.25; 435/7.1; 435/7.92; 435/326; 435/331

(58) Field of Classification Search ........................ None
See application file for complete search history.

(56) References Cited

U.S. PATENT DOCUMENTS

| | | | |
|---|---|---|---|
| 3,996,345 A | 12/1976 | Ullman et al. |
| 4,448,908 A | 5/1984 | Pauly et al. |
| 4,563,431 A | 1/1986 | Pauly et al. |
| 4,945,146 A | 7/1990 | Kapmeyer et al. |
| 5,183,766 A | 2/1993 | Kapmeyer |
| 5,340,716 A | 8/1994 | Ullman et al. |
| 5,545,834 A | 8/1996 | Singh et al. |
| 6,831,167 B2 | 12/2004 | Roemisch et al. |
| 2002/0142316 A1 | 10/2002 | Roemisch et al. |
| 2003/0124622 A1 | 7/2003 | Roemisch et al. |

FOREIGN PATENT DOCUMENTS

| | | |
|---|---|---|
| DE | 100 23 923 A1 | 12/2000 |
| EP | 0 080 614 A2 | 6/1983 |
| EP | 0 227 054 B2 | 7/1987 |
| EP | 0 246 446 B2 | 11/1987 |
| EP | 0 411 945 A2 | 2/1991 |
| EP | 0 515 194 A2 | 11/1992 |
| EP | 0 952 215 A2 | 10/1999 |
| EP | 1 182 258 A1 | 2/2002 |
| WO | WO 95/06877 | 3/1995 |
| WO | WO 95/25172 | 9/1995 |

OTHER PUBLICATIONS

Romisch et al., Haemostasis 29: 292-299 (1999); The FVII Activating Protease Cleaves Single-Chain Plasminogen Activators.

Willeit et al., Circulation 107, pp. 667-670 (2003), Marburg I Polymorphism of Factor VII—Activating Protease, A Prominent Risk Predictor of Carotid Stenosis.

Larrick et al., Human Antibodies and Hybridomas, 2: 172-189 (1991), "Recombinant Antibodies".

Bailey et al., Journal of Pharmaceutical & Biomedical Analysis 5: 649-658 (1987), "On The Use of Fluorescent Labels In Immunoassay".

Udenfriend et al., Proc. Natl. Acad. Sci. 82:8672-8676 (1985), "Scintillation Proximity Radioimmunoassay Utilizing I-Labeled Ligands".

Gerard Mathis, Clin Chem. 39(9): 1953-1959 (1993), "Rare Earth Cryptates and Homogeneous Fluoroimmunoassays With Human Sera".

Ullman et al., Clinical Chemistry 42(9): 518-1526(1996), "Luminescent Oxygen Channeling Assay (LOCI™): Sensitive, Broadly Applicable Homogeneous Immunoassay Method".

Ullman et al., Proc. Natl. Acad. Sci 91: 5426-5430 (1994), " Luminescent Oxygen Channeling Immunoassay: Measurement Of Particle Binding Kinetics By Chemiluminescence".

James P. Tam, Proc. Natl. Acad. Sci. USA 85: 5409-5413 (1988), "Synthetic Peptide Vaccine Design: Synthesis and Properties Of A High-Density Multiple Antigenic Peptide System".

McCafferty et al., Nature 348: 552-554 (1990), "Phage Antibodies: Filamentous Phage Displaying Antibody Variable Domains".

Kevin S. Johnson et al., Human Antibody Engineering, pp. 564-571 (1993), "Current Opinion In Structural Biology".

Kazuaki Kitano et al., Applied Microbiology and Biotechnology, 24: 282-286, (1986), "Production Of Human Monoclonal Antibodies By Heterohybridomas".

Keith M. Thompson et al., Journal of Immunological Methods 94: 7-12 (1986), "The Efficient Production Of Stable, Human Monoclonal Antibody-Secreting Hybridomas From EBV-Transformed Lymphocytes Using The Mouse Myeloma X63-Ag8.653 As A Fusion Partner".

Rainer Fischer et al., Biol Chem, vol. 380: 825-839 (1999), "Molecular Farming Of Recombinant Antibodies In Plants".

Andrew Hiatt et al., Genetic Engineering, vol. 14: 49-64 (1992), "Assembly Of Antibodies And Mutagenized Variants In Transgenic Plants And Plant Cell Cultures".

S. Shangary et al., "Peptides Derived from BH3 Domains of Bcl-2 Family Members: A Comparative Analysis of Inhibition of BCL-2, BCL-$x_L$ and Bax Oligomerization, Induction of Cytochrome *c* Release, and Activation of Cell Death," *Biochemistry*, 41: 9485-9495 (2002).

E. S. Burstein et al.,"Amino Acid Side Chains That Define Muscarinic Receptor/G-protein Coupling," *J. Biol.Chem.*, 271: 2882-2885 (1996).

J. Roemisch et al., "Quantitation of the Factor VII- and single-chain plasminogen activator-activating protease in plasmas of healthy subjects," *Blood Coag. and Fibrinol.*, 12: 375-383 (2001).

*Primary Examiner*—Michael Szperka
(74) *Attorney, Agent, or Firm*—Finnegan, Henderson, Farabow, Garrett & Dunner, L.L.P.

(57) ABSTRACT

The invention relates to antibodies which are directed against the FSAP Marburg I variant and to their preparation and use, in particular in therapy and diagnosis. The antibodies are characterized by the fact that they bind specifically to the FSAP MR I variant but not to the FSAP wild-type protein or other mutant variants which are characterized by amino acid substitutions at other positions in the FSAP protein.

10 Claims, No Drawings

SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Cys Glu Lys Arg
 1               5

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Val Tyr Gly Ile Val Ser Trp Gly Leu Glu Cys Glu Lys Arg Pro
 1               5                  10                  15

Gly Val Tyr Thr Gln Val Thr Lys Phe
             20                  25

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Trp Gly Leu Glu Cys Glu Lys Arg Pro Gly Val Tyr
 1               5                  10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Glu Phe His Glu
 1               5

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Asp Leu Lys Lys Glu Glu Phe His Glu Gln Ser Phe Arg Val
 1               5                  10                  15

```
-continued

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Trp Gly Leu Glu Cys Gly Lys Arg Pro Gly Val Tyr
 1               5                  10
```

ANTIBODIES WHICH ARE DIRECTED AGAINST THE MARBURG I POLYMORPHISM OF FACTOR VII-ACTIVATING PROTEASE (FSAP), AND THEIR PREPARATION AND USE

The invention relates to antibodies which are directed against the Marburg I polymorphism of the blood coagulation factor VII-activating protease (FSAP), and to their preparation and use.

The factor VII-activating protease (FSAP) is a plasma serine protease which, in addition to its property of activating blood coagulation factor VII also possesses plasminogen activator properties, that is prourokinase-activating properties [Roemisch et al. (1999) Haemostasis 76: 292-299; EP 952 216 A2]. This suggests that FSAP plays a role both 'in the blood coagulation cascade and in the fibrinolytic system.

FSAP is present in human plasma at a concentration of approx. 12 µg/ml and can be converted from the single-chain proenzyme into the active double-chain protease by means of autocatalysis. In addition to the wild-type sequence of the human FSAP gene, a variety of nucleotide polymorphisms are known, with these polymorphisms in two cases also leading to a change in the amino acid sequence (EP 1 182 258 A1). What is termed the Marburg I polymorphism (also MR I mutation, allele or variant) leads to a Gly/Glu amino acid substitution at position 534 of the proenzyme including the signal peptide (Gly/Glu 534) and results in a 50-80% reduction in the prourokinase-activating activity whereas the ability to activate factor VII remains unaltered. Another polymorphism, i.e. what is termed the Marburg II polymorphism (also MR II mutation, allele or variant) leads to a Glu/Gln amino acid substitution at position 370 of the proenzyme including the signal peptide (Glu/Gln 370). However, the Marburg II mutation has no effect on the prourokinase-activating activity of the FSAP. An MR I polymorphism is found in about 5% of the West-European population. Heterozygous carriers of the MR I polymorphism appear to be at a higher risk of developing a carotid stenosis than is the population on average [Willeit et al. (2003) Circulation 107: 667-670]. Consequently, FSAP, or the FSAP MR I variant, constitutes a potential marker for recognizing a disposition for atherosclerotic diseases.

In accordance with the prior art, it is possible to use a variety of methodological approaches for identifying individuals who are carrying at least one copy of the FSAP MR I variant (see EP 952 215 A1 and EP 1 182 258 A1). One of the known methods is based on determining the prourokinase-activating potential of the FSAP in a sample. To do this, a specific antibody, which is unable to distinguish between wild-type FSAP and the known FSAP variants, is coupled to a solid phase and incubated with the sample liquid. After prourokinase and chromogenic substrate have been added, the quantity of converted chromogenic substrate is determined as a measure of the prourokinase-activating activity of the FSAP. Carriers of the Marburg I polymorphism exhibit a prourokinase activity which is reduced by 50-80%. However, a reduction in prourokinase activity can also be due to the concentration of FSAP in the sample being low. It is therefore particularly advantageous to determine the FSAP antigen concentration in a sample in addition to the prourokinase activity. Monoclonal antibodies which enable FSAP to be detected immunologically are known from the prior art. EP 1 182 258 A1 describes two monoclonal antibodies which are derived from the hybridoma cell lines DSM ACC2453 and, respectively, DSM ACC2454 and which were obtained after immunizing mice with FSAP protein. Both the antibodies bind the Marburg I and II variants as well as the FSAP wild-type protein. Other known FSAP antibodies bind equally to wild-type FSAP and to the known mutant variants, which means that the total content of FSAP antigen in a sample can be determined in a sandwich ELISA, for example (see also DE 100 23 923 A1). A reduction in prourokinase activity is only a concrete indication of the presence of an FSAP MR I variant when this reduced activity is observed together with an FSAP antigen concentration which is in the normal range.

However, none of the described methods provides reliable proof of the presence of an FSAP MR I variant. However, in order to have recourse, for example, to appropriate prophylactic and therapeutic measures when the FSAP prourokinase activation potential is reduced, it is absolutely necessary to diagnose the cause of the loss of function accurately.

It has thus far only been possible to detect the Gly/Glu amino acid substitution at position 534 of the proenzyme (Gly/Glu 534) unambiguously by sequencing the corresponding coding region in the genomic DNA or the mRNA. A G/A base substitution in the genomic sequence, which can be detected at nucleotide position 1601 in the cDNA, is the genetic cause of the FSAP MR I polymorphism (see EP 1 182 258 A1). Even if the DNA sequence analysis provides reliable results, the routine laboratory has a need for established test methods which are as economic, reliable and rapid—as possible and which, in addition, can be implemented automatically on available diagnostic equipment. Preference is given, in the main, to immunological detection methods or test assays since they meet known criteria and are already used widely in laboratory diagnostics.

The present invention was therefore based on the object of providing a method and/or components which make it possible to specifically detect the FSAP MR I variant using antibodies.

This object is achieved by the provision of the methods and objects according to the invention which are described in the claims.

In particular, the object is achieved by the provision of antibodies which bind specifically to the FSAP MR I variant but not the FSAP wild-type protein or other mutant variants which are not characterized by a Gly/Glu amino acid substitution at position 534 in the FSAP proenzyme. These antibodies form the basis for the direct immunological detection and quantification of the FSAP MR I variant in plasma samples from heterozygous carriers or homozygous individuals.

It has been found, surprisingly, that peptides which comprise at least the amino acid sequence Glu-Cys-Glu-Lys-Arg (SEQ ID NO:1), which corresponds to amino acids 532 to 536 in the FSAP MR I variant and consequently comprises the Gly/Glu amino acid substitution at position 534 of the proenzyme (Gly/Glu 534), are suitable for use as immunizing antigens for preparing FSAP MR I-specific antibodies. The peptides according to the invention are distinguished by the fact that the FSAP MR I-specific Glu residue at position 534 is flanked, both N-terminally and C-terminally, by at least two further amino acid residues.

Specific embodiments of the invention are explained in more detail below:

One part of the subject matter of this invention is represented by peptides which comprise from 5 to 25 amino acids, such as from 5 to 20 amino acids, or such as from 10 to 15 amino acids, and which are characterized in that they comprise the amino acid sequence Glu-Cys-Glu-Lys-Arg (SEQ ID NO:1). In some embodiments of the invention, peptides comprise the amino acid sequence Tyr-Val-Tyr-Gly-Ile-Val-Ser-Trp-Gly-Leu-Glu-Cys-Glu-Lys-Arg-Pro-Gly-Val-Tyr- Thr-Gln-Val-Thr-Lys-Phe (SEQ ID NO:2) or a fragment thereof which comprises at least the amino acid sequence Glu-Cys-Glu-Lys-Arg (SEQ ID NO:1), such as a peptide comprising the amino acid sequence Ser-Trp-Gly-Leu-Glu-Cys-Glu-Lys-Arg-Pro-Gly-Val-Tyr (SEQ ID NO:3).

Within the meaning of this invention, the term "peptides" encompasses acid amides which decompose into amino acids on hydrolysis, for example amino acid polymers such as polypeptides, oligopeptides, proteins or protein fragments.

The peptides according to the invention can be used as immunizing antigen for preparing the antibodies according to the invention or else for purifying the antibodies according to the invention by means of affinity chromatography. Furthermore, the peptides according to the invention can also be used in a method for quantitatively or qualitatively detecting an analyte, preferably the FSAP MR I variant. The peptides according to the invention can also be linked to, a solid phase and/or a component of a signal-generating system.

One aspect of the invention is represented by antibodies that bind to the characterizing epitope of the FSAP MR I variant, i.e. to the amino acid sequence Ser-Trp-Gly-Leu-Glu-Cys-Glu-Lys-Arg-Pro-Gly-Val-Tyr (SEQ ID NO:3), which corresponds to amino acids 528-540 in the FSAP MR I variant.

Within the meaning of this invention, the term "antibody" is to be understood as signifying an immunoglobulin, for example an immunoglobulin of the IgA, IgD, IgE, $IgG_1$, $IgG_{2a}$, $IgG_{2b}$, $IgG_3$, $IgG_4$ or IgM class or subclass. An antibody possesses at least one binding site (frequently termed paratope) for an epitope (frequently also termed antigenic determinant) on an antigen or hapten. Such an epitope is characterized, for example, by its spatial structure and/or the presence of polar and/or apolar groups. The binding site of the antibody is complementary to the epitope. The antigen-antibody reaction or the hapten-antibody reaction functions in accordance with what is termed the "key-keyhole principle" and is as a rule highly specific, i.e. the antibodies are able to distinguish small differences in the primary structure, in the charge, in the spatial configuration and in the steric arrangement of the antigen or hapten. In particular, what are termed the "complementarity-determining regions" of the antibody contribute to binding the antibody to the antigen or hapten.

The term "antigens" encompasses monovalent and polyvalent antigens. A polyvalent antigen is a molecule or a molecular complex to which more than one immunoglobulin is able to bind simultaneously whereas only one single antibody can bind at any one time to a monovalent antigen. A hapten is usually the name given to a molecule which is not immunogenic on its own but which, for immunization purposes, is usually bound to a carrier.

Within the meaning of this invention, the term antibodies is to be understood as signifying not only complete antibodies but also, expressly, antibody fragments such as Fab, Fv, F(ab')$_2$ and Fab'; as well as chimeric, humanized, bispecific or oligospecific, or single-chain antibodies; and, in addition, also aggregates, polymers and conjugates of immunoglobulins and/or their fragments provided their properties with regard to binding to the antigen or hapten are retained. Antibody fragments can be prepared, for example, by cleaving antibodies enzymatically with enzymes such as pepsin or papain. Antibody aggregates, antibody polymers and antibody conjugates can be generated by many different methods, for example by heat treatment, by reaction with substances such as glutaraldehyde, by reaction with immunoglobulin-binding molecules, by biotinylation of antibodies and subsequent reaction with streptavidin or avidin, etc.

Within the meaning of this invention, an antibody can be a monoclonal antibody or a polyclonal antibody. The antibody can have been prepared in accordance with the customary methods, for example by immunizing the human subject or an animal, such as a mouse, a rat, guinea pig, rabbit, horse, donkey, sheep, goat or hen also Messerschmid (1996) BIO-forum 11: 500-502], 'and then isolating the antiserum; or by, establishing hybridoma cells and subsequently purifying the secreted antibodies; or by cloning and expressing the nucleotide sequences, or modified versions thereof, which encode the amino acid sequences which are responsible for the binding of the natural antibody to the antigen and/or hapten.

Antibodies according to the invention include, for example, antibodies which bind to a peptide of from 5 to 25 amino acids, such as from 5 to 20 amino acids, or such as from 10 to 15 amino acids, and which comprises the FSAP MR I-specific amino acid sequence Glu-Cys-Glu-Lys-Arg (SEQ ID NO:1). Some antibodies of this invention bind specifically to peptides comprising the amino acid sequence Ser-Trp-Gly-Leu-Glu-Cys-Glu-Lys-Arg-Pro-Gly-Val-Tyr (SEQ ID NO:3) or to a fragment of this peptide which comprises at least the amino acid sequence Glu-Cys-Glu-Lys-Arg (SEQ ID NO:1).

The antibodies which are produced by the hybridoma cell lines a) Mab (mouse) directed against ECE-KLH 2004-9/014 (1), b) Mab (mouse) directed against ECE-KLH 2004-9/026 (2), c) Mab (mouse) directed against ECE-KLH 2004-35/05 (1), d) Mab (mouse) directed against ECE-KLH 2004-34/08 (2) or e) Mab (mouse) directed against ECE-KLH 2004-151/013 (2)

are also embodiments of this invention. The hybridoma cell lines a) to c) were deposited on Aug. 11, 2004 in the DSMZ—Deutsche Sammlung von Mikroorganismen und Zellkulturen [German collection of microorganisms and cell cultures] GmbH, MascheroderWeg 1b, 38124 Braunschweig, Germany, under the receipt numbers a) DSM ACC2675 b) DSM ACC2676 and c) DSM ACC2674. The hybridoma cell lines d) and e) were deposited on May 19, 2005 in the abovementioned depository institution under the receipt numbers d) DSM ACC2725 and e) DSM ACC2726.

Another part of the subject matter of this invention relates to specific binding partners which bind to an epitope which is recognized by an antibody according to the invention.

A "specific binding partner" is to be understood as being a member of a specific binding pair. The members of a specific binding pair are two molecules which in each case possess at least one structure which is complementary to a structure of the other molecule, with the two molecules being able to bind to each other by means of the complementary structures binding. The term molecule also encompasses molecular complexes such as enzymes which consist of apoenzyme and coenzyme, proteins which consist of several subunits, lipoproteins which consist of protein and lipids, etc. Specific binding partners can be naturally occurring substances or else substances which are, for example, prepared by means of chemical synthesis, microbiological techniques and/or recombinant methods. The following may, for example, be mentioned in order to illustrate the term specific binding partner but without this being understood as a limitation: thyroxine-binding globulin, steroid-binding proteins, antibodies, antigens, haptens, enzymes, lectins, nucleic acids, repressors, oligonucleotides and polynucleotides, protein A, protein G, avidin, streptavidin, biotin, complement component Clq, nucleic acid-binding proteins, etc. Examples of specific binding pairs are: antibody-antigen, antibody-hapten, operator-repressor, nuclease-nucleotide, biotin-avidin, lectin-polysaccharide, steroid-steroid-binding protein, active compound-active compound receptor, hormone-hormone receptor, enzyme-substrate, IgG-protein A, complementary oligonucleotides or polynucleotides, etc.

As a result of providing the antibodies according to the invention, it is now possible for the skilled person, for example by means of competition experiments (see also Peters et al. (1985) Monoklonale Antikörper [Monclonal Antibodies], Springer Verlag, Chapter 12.2 "Epitope analysis"], to identify other specific binding partners, with antibodies being expressly included, which bind to the epitope of an antibody according to the invention. Thus, specific binding partners can by now be selected using phage display libraries, by way of synthetic peptide databases, or using recombinatorial antibody libraries [Larrick & Fry (1991) Human Antibodies and Hybridomas 2: 172-189].

This invention also relates to an antibody according to the invention which is linked to a solid phase and/or a component of a signal-generating system.

Within the meaning of this invention, the term "solid phase" means an object which consists of a porous and/or nonporous, as a rule water-insoluble, material and can have a very wide variety of forms, for example those of vessels, tubes, microtitration plates, spheres, microparticles, rods, strips, filter paper, chromatography paper, etc. As a rule, the surface of the solid phase is hydrophilic or can be made hydrophilic. The solid phase can consist of a very wide variety of materials, for example of inorganic and/or organic materials, of synthetic materials, of naturally occurring materials and/or of modified naturally occurring materials. Examples of solid phase materials are polymers, such as cellulose, nitrocellulose, cellulose acetate, polyvinyl chloride, polyacrylamide, crosslinked dextran molecules, agarose, polystyrene, polyethylene, polypropylene, polymethacrylate or nylon; ceramic, glass or metals, in particular precious metals such as gold and silver; magnetite; mixtures or combinations thereof; etc. Cells, liposomes and phospholipid vesicles are also covered by the term solid phase.

The solid phase can also possess a coating consisting of one or more layers, for example of proteins, carbohydrates, lipophilic substances, biopolymers or organic polymers, or mixtures thereof, in order, for example, to suppress or prevent the nonspecific binding of sample constituents to the solid phase or in order, for example, to achieve improvements with regard to the suspension stability of particular solid phases, with regard to storage stability, with regard to dimensional stability or with regard to resistance to UV light, microbes or other agents having a destructive effect.

A "signal-generating system" can be one or more components with at least one of the components being a detectable label. A label is to be understood as being any molecule which itself produces a signal or which is able to induce the production of a signal, for example a fluorescent substance, a radioactive substance, an enzyme or a chemiluminescent substance. The signal can, for example, be detected or measured using the enzyme activity, the luminescence, the light absorption, the light scattering, the emitted electromagnetic or radioactive radiation or a chemical reaction.

A label may itself be able to generate a detectable signal, such that no further components are required. Many organic molecules absorb ultraviolet and visible light, resulting in these molecules being able to reach an excited energy state and to emit the absorbed energy in the form of light which is of a different wavelength from that of the incident light. Yet other labels can directly generate a detectable signal, for example radioactive isotopes or dyes.

Yet other labels require additional components for generating the signal, i.e., in such a case, the signal-producing system includes all the components, such as substrates, coenzymes, quenchers, accelerators, additional enzymes, substances which react with enzyme products, catalysts, activators, cofactors, inhibitors, ions, etc., which are required for producing the signal.

Examples of suitable labels [see also EP 0 515 194 A2; U.S. Pat. No. 5,340,716; U.S. Pat. No. 5,545,834; Bailey et al. (1987) J. Pharmaceutical & Biomedical Analysis 5: 649-658] are enzymes, including horseradish peroxidase, alkali phosphatase, glucose 6-phosphate dehydrogenase, alcohol dehydrogenase, glucose oxidase, β-galactosidase, luciferase, urease and acetylcholine esterase; dyes; fluorescent substances, including fluorescein isothiocyanate, rhodamine, phycoerythrin, phycocyanine, ethidium bromide, 5-dimethylamino-naphthalene-1-sulfonyl chloride and fluorescent chelates of rare earths; chemiluminescent substances including luminol, isoluminol, acridinium compounds, olefin, enolether, enamine, arylvinylether, dioxene, arylimidazole, lucigenin, luciferin and aequorin; sensitizers, including eosin, 9,10-dibromoanthracene, methylene blue, porphyrin, phthalocyanine, chlorophyll and Rose Bengal; coenzymes; enzyme substrates; radioactive isotopes, including $^{125}I$, $^{131}I$ $^{14}C$, $^{3}H$, $^{32}P$, $^{35}S$, $^{14}C$, $^{51}Cr$, $^{59}Fe$, $^{57}Co$ and $^{75}Se$; particles, including magnetic particles or particles, preferably latex particles, which themselves can be labeled with, for example, dyes, sensitizers, fluorescent substances, chemiluminescent substances, isotopes or other detectable labels; sol particles including gold sols or silver sols; liposomes or cells which can themselves be labeled with detectable labels; etc.

A signal-generating system can also comprise components which, when in spatial proximity to each other, are able to enter into a detectable interaction, for example components in the form of energy donors and energy recipients, such as photosensitizers and chemiluminescent substances (EP 0 515 194 A2), photosensitizers and fluorophores (WO 95/06877), radioactive iodide$^{125}$ and fluorophores [Udenfriend et al. (1985) Proc. Natl. Acad. Sci. 82: 8672-8676], fluorophores and fluorophores [Mathis (1993) Clin. Chem. 39: 1953-1959] or fluorophores and fluorescence quenchers (U.S. Pat. No. 3,996,345). An interaction between components also includes the direct transfer of energy between the components, for example by means of light radiation or electron radiation and also by way of short-lived reactive chemical molecules. Interactions also include processes in which the activity of a component is inhibited or augmented by one or more other components, for example the inhibition of, or increase in, the enzyme activity or the inhibition of, increase in or change in (e.g. wavelength shift, polarization) the electromagnetic radiation which is emitted by the affected component. The interaction between the components also includes enzyme cascades. In this case, the components are enzymes at least one of which provides the substrate for another, thereby resulting in the coupled substrate reaction taking place at a maximum or minimum reaction rate. As a rule, an effective interaction between the components takes place when the components are spatially adjacent to each other, that is, for example, within a distance range of a few μm, in particular within a distance range of less than 600 nm, preferably less than 400 nm, very particularly preferably less than 200 nm.

Microparticles are frequently used as the solid phase and/or the label. Within the meaning of this invention, the term "microparticles" is to be understood as signifying particles which have an approximate diameter of less than 20 nm and not more than 20 μm, customarily between 40 nm and 10 μm, such as between 0.1 and 10 μm, between 0.1 and 5 μm, or between 0.15 and 2 μm. The microparticles can have a regular or irregular shape. They can be spheres, spheroids or spheres having cavities or pores of greater or lesser size. The microparticles can also comprise organic material or inorganic material or a mixture or combination of the two. They can comprise a porous or nonporous, a swellable or nonswellable material. While, in principle, the microparticles can be of any density, some particles used in the invention have a density, such as from about 0.7 to about 1.5 g/ml, which approaches the density of water. The microparticles can be suspended in aqueous solutions, with their suspensions being stable for as long as possible. It is possible for them to be transparent, partially transparent or nontransparent. The microparticles can comprise several layers such as, for example, what are termed core-and-shell particles having a core and one or more enveloping layers.

The term microparticles encompasses, for example, dye crystals, metal sols, silica particles, glass particles, magnetic particles, polymeric particles, oil drops, lipid particles, dextran and protein aggregates. In some embodiments, microparticles can be suspended in aqueous solutions and comprise water-insoluble polymer material, such as substituted polyethylenes. In some embodiments, microparticles comprise latex particles of, for example, polystyrene, acrylic acid polymers, methacrylic acid polymers, acrylonitrile polymers, acrylonitrile-butadiene-styrene, polyvinyl acetate-acrylate, polyvinylpyridine or vinyl chloride-acrylate. In some embodiments, latex particles possess reactive groups, such as carboxyl, amino or aldehyde groups, at their surface, with these groups enabling specific binding partners, for example, to be bonded covalently to the latex particles. The preparation of latex particles is described, for example, in EP 0 080 614, EP 0 227 054 and EP 0 246 446.

The term "linked" is to be understood in a broad manner and encompasses, for example, a covalent bond and a noncovalent bond, a direct linkage and an indirect linkage, adsorption to a surface and inclusion in an invagination or a cavity, etc. In the case of a covalent bond, the antibodies or binding partners are bound to the solid phase or to the label by way of a chemical bond. Examples of a noncovalent bond are surface adsorption, inclusion in cavities or the binding of two specific binding partners. In addition to a direct linkage to the solid phase or the label, the antibodies or binding partners can also be bound indirectly to the solid phase or the label by way of specific interaction with other specific binding partners (see also EP 0 411 945 A2). This will be illustrated in more detail with the aid of examples: the biotinylated antibody can be bound to the label by way of label-bound avidin, or a fluorescein-antibody conjugate can be bound to the solid phase by way of solid phase-bound anti-fluorescein antibodies, or the antibody can be bound to the solid phase or the label by way of immunoglobulin-binding proteins.

This invention furthermore relates to specific binding partners or antibodies according to the invention which are used as an in-vitro diagnostic agent or as a constituent of an in-vitro diagnostic agent. In the case of an in-vitro diagnostic agent, the analyte to be detected, e.g. the FSAP Marburg I variant, is detected, or its concentration or quantity is determined, in a sample outside a living human or animal body.

Within the meaning of the invention, a "sample" is to be understood as signifying the material which is suspected of containing the substance to be detected (for examples of the term "analyte", see EP 0 515 194 A2, pages 8-15). The term sample encompasses, for example, biological fluids or tissues from humans and animals, in particular, such as blood, plasma, serum, sputum, exudate, bronchoalveolar lavage, lymph fluid, synovial fluid, seminal fluid, vaginal mucus, feces, urine, cerebral spinal fluid, hair, skin and tissue samples or sections. It also encompasses cell culture samples, plant liquids or tissues, forensic samples, water and effluent samples, nutrients and pharmaceuticals. Where appropriate, the samples have to be pretreated in order to make the analyte accessible to the detection method or in order to remove interfering sample constituents. Such a pretreatment of samples may involve separating off and/or lysing cells, precipitation, the hydrolysis or denaturation of sample constituents such as proteins, the centrifugation of samples, the treatment of the sample with organic solvents such as alcohols, in particular methanol; and the treatment of the sample with detergents. The sample is frequently transferred into another, usually aqueous, medium, which will, if at all possible, not interfere with the detection method.

The antibodies according to the invention can be used in a method for quantitatively or qualitatively detecting an analyte, preferably the FSAP Marburg I variant, in a sample.

In the case of a quantitative detection, the quantity, the concentration or the activity (e.g. enzyme activity) of the analyte in the sample is measured. The term "quantitative detection" also includes semi-quantitative methods which are only able to detect the approximate quantity, concentration or activity of the analyte in the sample or are only able to be used to give a relative indication of the quantity, concentration or activity. A qualitative detection is to be understood as detecting whether the analyte is at all present in the sample or indicating that the concentration or activity of the analyte in the sample is below or above one particular threshold value or several particular threshold values.

The invention consequently also relates to methods for quantitatively or qualitatively detecting an analyte, preferably FSAP Marburg I variant, in a sample, and to reagents which are suitable for this purpose.

Binding tests in which the specific binding of analyte to be detected to analyte-specific binding partners can be used to draw conclusions with regard to the presence, absence or quantity of the analyte in a sample are frequently employed for detecting analytes. Immunoassays or methods in which oligonucleotides or polynucleotides are hybridized are examples of binding tests.

What are termed "heterogeneous binding tests" are characterized by one or more separation steps and/or washing steps. The separation can be effected, for example, by means of immunoprecipitation, precipitation with substances such as polyethylene glycol or ammonium sulfate, filtration, magnetic separation, or binding to a solid phase. Such a "solid phase" consists of porous and/or nonporous, as a rule water-insoluble, material. It can have a very wide variety of different forms, such as that of vessels, tubes, microtitration plates, spheres, microparticles, rods, strips, filter paper or chromatography paper, etc. In the case of heterogeneous binding tests in sandwich format, one of the analyte-specific binding partners is as a rule bound to a solid phase and serves for separating off the "analyte/analyte-specific binding partner" binding complex from the liquid phase while the other analyte-specific binding partner carries a detectable label, e.g. an enzyme, or a fluorescence or chemiluminescene label, etc., for detecting the binding complex. These test methods are further subdivided into what are termed one-step sandwich tests, in which the two specific binding partners are incubated simultaneously with the sample, and into two-step sandwich tests, in which the sample is first of all incubated with the solid-phase reagent and, after a separation and washing step, the solid phase-bound binding complex composed of analyte and analyte-specific binding partner is incubated with the detection reagent.

In the case of "homogeneous binding tests", the components of the signal-generating system which are bound to the "analyte/analyte-specific binding partner" complex and those which are free are not separated. The test mixture, which contains the analyte-specific binding partners, the signal-generating components and the sample, is measured, and the corresponding measurement signal determined, after, or even during, the binding reaction without any further separation and/or washing step. Many turbidimetric or nephelometric methods, in which the analyte-specific binding partners employed for the detection can be linked to latex particles, such as EMIT® tests; CEDIA® tests; fluorescence-polarization immunoassays; luminescent oxygen channeling immunoassays [LOCI®, see EP 0 515 194 A23; Ullman et al. (1994) Proc. Natl. Acad. Sci. 91: 5426-5430; Ullman et al. (1996) Clinical Chemistry 42: 1518-1526] etc., are examples of homogeneous immunoassays [see also Boguslaski & Li (1982) Applied Biochemistry and Biotechnology 7: 401-414]. In a homogeneous sandwich immunoassay, such as a nephelometric latex test, the antibody reagents are incubated with the sample and the signal is measured during and/or after the incubation without a separation or washing step being carried out prior to the measurement. Expressed in other words: the antibody-bound analyte is not separated from the free analyte or from antibodies which have not bound any analyte.

The antibodies according to the invention are particularly suitable for use in homogeneous binding tests.

Homogeneous and heterogeneous binding tests can also be carried out in the form of what is termed a "sandwich assay". In this case, the analyte is, for example in the case of a heterogeneous binding test, bound by a solid phase-linked, analyte-specific binding partner and by an analyte-specific binding partner which is linked to a component of a signal-generating system. In sandwich immunoassays, antibodies or antigens or haptens can be the analyte-specific binding partners.

The "indirect immunoassay" is another special embodiment of a heterogeneous or homogeneous binding test. In this case, the analyte is an antibody. One of the analyte-specific binding partners is the antigen or, for example, the peptides according to the invention, or a modified antigen of the antibody to be detected (=analyte), and the other analyte-specific binding partner is as a rule an immunoglobulin-binding protein such as an antibody which is able to specifically bind the antibody to be detected (=analyte).

In a homogeneous or heterogeneous "competitive binding test", sample analyte and reagent analyte compete for binding to a limited number of analyte-specific binding partners. The reagent analyte is, for example, a "modified analyte" such as a labeled analyte, an analyte fragment, such as the peptides according to the invention, or an analyte analog. The following examples illustrate the principle: (i) sample analyte competes with reagent analyte, which is linked with a component of a signal-generating system, for binding to solid phase-linked, analyte-specific binding partners, or (ii) sample analyte competes with solid phase-linked analyte (=reagent analyte) for binding to analyte-specific binding partners which are linked to a component of a signal-generating system.

The antibodies according to the invention can also be used to detect the FSAP Marburg I variant employing methods such as Western blotting, dot blotting, immunoelectrophoresis, immunofixation electrophoresis, electroimmunodiffusion, immunoprecipitation, radial immunodiffusion, immunofixation, immunochromatography, latex agglutination, turbidimetric or nephelometric test, homogeneous or heterogeneous binding test, one-step or two-step test, sandwich test, indirect test, competitive test, point-of-care tests, etc. These, and other, detection methods are described, for example, in "Labor und Diagnose [Laboratory and Diagnosis]", ed. L. Thomas, TH-Books Verlagsgesellschaft mbH, Frankfurt, 1998, chapter 60, or in "Laboratory Techniques in Biochemistry and Molecular Biology—An Introduction to Radioimmunoassay and Related Techniques", ed. T. Chard, Elsevier, Amsterdam, 1987.

The term "point-of-care tests" or "POC tests" encompasses tests in which no separate analytical or measuring equipment is required for carrying out the test or evaluating the test. In many cases, POC tests are based on immunochromatographic methods, immunocomplex separation by means of filtration and/or immunofixation techniques. POC tests are intended, in particular, for measurements carried out on the spot, for example at the patient's bedside or at home, and for the emergency doctor and/or the registered physician and less for the large laboratory. POC tests can, in particular, also be carried out by individuals who do not have any detailed medical training and experience in the field of laboratory medicine. Within the meaning of this invention, the term "POC tests" is also to be understood as including what are termed home tests or OTC tests which may be carried out by medical lay persons, such as, for example, the various pregnancy tests which are marketed for use at home. Other POC tests relate, for example, to detecting cardiac infarction markers, drugs, pharmaceuticals, infection markers and inflammation markers. In many POC tests, specific binding partners are linked, or become linked during the course of implementing the test, to or on filter or chromatographic strips or discs. A positive or negative detection reaction can, for example, be linked to the appearance or nonappearance of a color band in a particular test field and/or the appearance or nonappearance of a particular symbol, for example a "+" or a "−" and/or the intensity of the respective measurement signal.

A POC test for the FSAP Marburg I variant can, for example, be set up as follows: the sample and labeled antibodies which are able to bind to the FSAP Marburg I variant but not to wild-type FSAP or other FSAP variants are loaded onto a test strip. Examples of suitable labels are colored latex particles, colloidal gold, enzymes, etc. If the FSAP Marburg I variant is present in the sample, FSAP MR I/antibody complexes will be formed. These complexes move, for example by means of capillary forces, in the direction towards a region in which antibodies which are able to bind to other FSAP MR I epitopes, and which are fixed, or become fixed during the course of the test procedure (e.g. by way of a biotin-avidin bridge), for example in the form of a band, are located. The labeled FSAP MR I/antibody complexes are bound in this region and form a sandwich complex together with the fixed antibodies. In this case, the intensity of the label signal is proportional to the concentration of FSAP MR I in the sample. In the case of a competitive POC test method, antibody fragments can, for example, be fixed, or become fixed during the course of the test procedure, in a region of the test strip. This fixed antibody would compete with the FSAP Marburg, I variant from the sample for binding to labeled anti-FSAP MR I antibodies. Alternatively, fixed anti-FSAP Marburg I variant antibodies and labeled FSAP MR I protein, or the peptides according to the invention, can also be employed for setting up a competitive FSAP Marburg I variant test.

One embodiment of the method according to the invention is a nephelometric or turbidimetric test, for instance, a test which employs antibodies according to the invention, optionally linked to a solid phase such as microparticles (including latex particles).

Another part of the subject matter of the invention is a test kit which comprises one or more of the antibodies and/or peptides according to the invention. Such a kit customarily comprises all or only some components of a test in packaged form. The antibodies and/or peptides according to the invention can, for example, be linked to one or more solid phases and/or one or more components of a signal-generating system. The test kit can, for example, comprise standards, controls, calibrators and other reagents, such as buffers, washing solutions, measurement signal-initiating solutions and/or enzyme substrate, cuvettes, pipettes and/or test instructions.

Reconstitutable lyophilized preparations, such as liquid preparations which either contain a defined quantity of FSAP Marburg I protein in a native or recombinant form or a defined quantity of a peptide according to the invention which comprises the amino acid sequence Glu-Cys-Glu-Lys-Arg (SEQ ID NO:1) are suitable for use as standards, controls or calibrators in methods for quantitatively or qualitatively detecting the FSAP Marburg I variant using specific binding partners. Molecules comprising a peptide moiety of from 5 to 25 amino acids comprising the amino acid sequence Glu-Cys-Glu-Lys-Arg (SEQ ID NO:1) as well as another moiety of from 5 to 15 amino acids and which comprises the amino acid sequence Glu-Glu-Phe-His-Glu (SEQ ID NO:4) are likewise suitable. The latter peptide moiety may comprise the amino acid sequence Gln-Asp-Leu-Lys-Lys-Glu-Glu-Phe-His-Glu-Gln-Ser-Phe-Arg-Val (SEQ ID NO:5) or of a fragment thereof comprising the sequence Glu-Glu-Phe-His-Glu (SEQ ID NO:4). The amino acid sequence Glu-Glu-Phe-His-Glu (SEQ ID NO:4) corresponds to the amino acid positions 383 to 387 in the FSAP proenzyme and represents an epitope which is present both in the wild-type FSAP protein and in the FSAP Marburg I variant. Since the fusion peptides according to the invention are bound both by binding partners having specificity for the FSAP Marburg I polymorphism, for example, by the antibodies according to the invention, and by binding partners having specificity for the Glu-Glu-Phe-His-Glu-containing epitope of the FSAP proenzyme, for example by monoclonal antibodies which are formed by the hybridoma cell line which was deposited in the DSMZ—Deutsche Sammlung von Mikroorganismen and Zellkulturen [German collection of microorganisms and cell cultures] GmbH in Braunschweig, Germany, under the receipt number DSM ACC2453 (see EP 1 182 258 A1), they are particularly suitable for standardizing, calibrating or controlling quantitative or qualitative sandwich test methods. The fusion peptides can be prepared by means of an appropriate peptide synthesis. It is likewise possible to link the FSAP Marburg I epitope and the wild-type epitope together using homobifunctional crosslinkers such as glutaraldehyde or bi-NHS esters or using heterobi-functional crosslinkers such as N-hydroxysuccinimide (NHS)-X-maleimide or NHS-X-haloacetyl, N-γ-maleimidobutyryloxysuccinimide ester (GMBS), N-succinimidyl (4-iodoacetyl) aminobenzoate (SIAB) and heterobifunctional reagents which generate a free SH group, such as iminothiolane, N-succinimidyl S-acetylthioacetate (SATA), N-succinimidyl 3-(2-pyridyldithio) propionate (SPDP) or 4-succinimidyloxycarbonyl-methyl-α-(2-pyridyldithio) toluene (SMPT), or to conjugate the two epitopes with a shared carrier, such as ovalbumin, albumin, keyhold limpet hemocyanin (KLH) or bovine alpha-lactalbumin, as well as polymers such as dextran, polyethylene glycol, polyacrylamide or poly-d-glutamine-d-lysine, etc. The peptide can, for example, be bound to these carriers using carbodiimide or glutaraldehyde or else using a heterobifunctional reagent, such as N-maleimidobutyryl-oxysuccinimide ester (GBMS), which can also act as a spacer. For further examples and for coupling methods, see also Wong, S. (1993) Chemistry of Protein Conjugation and Cross-Linking, CRC Press Inc., Boca Raton.

One test kit according to the invention comprises antibodies according to the invention and/or peptides according to the invention which are linked to latex particles.

Another test kit according to the invention comprises a plasma product which consists of a pool of at least five, preferably of more than 20, human plasmas from heterozygous FSAP Marburg I donors. Heterozygous donors can be identified using known screening methods (see EP 1 182 258 A1) and, naturally, also using the antibodies according to the invention. Such an FSAP Marburg I plasma pool can be used, for example, as a standard, with a reference value, such as 100% or 1 PEU (plasma equivalent units)/ml, being defined for the pool. Such a pool, or different dilutions of the plasma pool, can be used for setting up substandards (e.g. peptide standards) or for defining a cut-off value and a gray region, which may possibly be required, for detecting the FSAP Marburg I variant antigen.

The antibodies and the peptides according to the invention can also be used for affinity chromatography. The term "affinity chromatography" is to be understood as meaning a method for purifying and isolating substances, in particular biopolymers, which is based on the fact that many substances are able to enter into a selective, noncovalent, reversible binding with binding partners which are specific for them. The principle of the method is that the specific binding partner is bonded, as a rule covalently, to an insoluble matrix (e.g. porous glasses, or gels based on agarose, cellulose, dextran, polymer or silica) and brought into contact with a sample which contains the substance. Due to its specific interaction with the matrix-bonded specific binding partner, the sought-after substance is immobilized and retained while all the other substances present in the sample are separated off by elution. The sought-after substance is then released from the matrix using a suitable eluent which abolishes the noncovalent bond between the substance and the specific binding partner (see also E. Buddecke, 1989, Grundrisse der Biochemie [Outlines of biochemistry], Walter de Gruyter, chapter 7 "Proteine [Proteins]").

Another part of the subject matter of this invention encompasses antibodies according to the invention or peptides according to the invention in a pharmaceutically tolerated, sterile injection medium. A pharmaceutically tolerated, sterile injection medium is to be understood, for example, as being an organism-free, pyrogen-free solution, for example saline or another electrolyte solution as is customarily used for the intravenous, intramuscular, intraperitoneal or subcutaneous administration of pharmaceuticals, vaccines or contrast agents.

Yet another part of the subject matter of this invention is the use of the antibodies according to the invention as a diagnostic agent or as a constituent of a diagnostic agent.

Another part of the subject matter of this invention is a method for preparing an antibody according to the invention, which method is characterized in that one or more peptides of from 5 to 25 amino acids, such as from 5 to 20 amino acids, or such as from 10 to 15 amino acids, and which comprise the amino acid sequence Glu-Cys-Glu-Lys-Arg (SEQ ID NO: 1) are used for the immunization. The immunizing antigens which comprise this method according to the invention are peptides which have the amino acid sequence Ser-Trp-Gly-Leu-Glu-Cys-Glu-Lys-Arg-Pro-Gly-Val-Tyr (SEQ ID No: 3)

or fragments which at least comprise the amino acid sequence Glu-Cys-Glu-Lys-Arg (SEQ ID NO: 1).

The antibodies according to the invention can also be prepared by using naturally occurring and/or recombinant FSAP MR I protein, or fragments thereof, which contain the FSAP MR I-specific polymorphism.

The peptides which are used as immunizing antigens can be used for the immunization in unbound form and/or in carrier-bound form.

Examples of typical carriers are proteins, such as ovalbumin, albumin or keyhole limpet hemocyanin (KLH), or polymers, such as polyethylene glycol, polyacrylamide or poly-d-glutamine-d-lysine. The peptides can, for example, be bonded to these carriers using carbodiimide or glutaraldehyde or else using a heterobifunctional reagent, such as N-maleimidobutyryl-oxysuccinimide ester (GBMS), which can also act as a spacer. For further examples and coupling methods, see also Wong, S. (1993) Chemistry of Protein Conjugation and Cross-Linking, CRC Press, Inc., Boca Raton.

A preferred method for preparing the peptides according to the invention which are used, inter alia, as immunizing antigens is that of solid-phase synthesis, with a multiplicity of copies of a peptide being synthesized on a lysine nucleus [see also Tam J. P. (1988) Proc. Natl. Acad. Sci. USA 85: 5409-5413]. The peptide synthesis is preferably carried out in accordance with a standard protocol and using automated equipment as is offered for sale, for example, by Applied Biosystems (USA). These multimeric peptides can subsequently be bonded to a carrier protein.

The immunizing antigen can, for example, be taken up in phosphate-buffered saline and treated with Immune Easy Mouse Adjuvant. This emulsion can then be administered, for example intradermally, intraperitoneally and/or subcutaneously, to an animal, for example a rabbit, a mouse, a rat, a guinea pig, a horse, a donkey, a sheep, a goat, a chicken, etc. Booster injections, with it also being possible to emulsify the immunizing antigen with incomplete Freund's adjuvant, may help to increase the immune response.

Polyclonal antibodies according to the invention can be isolated from the antiserum of the immunized animals and can be further purified by means of an affinity chromatography through a matrix to which, for example, the FSAP Marburg I variant or the peptides employed as immunizing antigen has/have been bonded.

In order to produce monoclonal antibodies according to the invention, the immune cells of immunized animals, such as a mouse or a rabbit, are, in accordance with the well-known methods [see also Harlow & Lane (1988) Antibodies: A Laboratory Manual, Cold Spring Harbor Laboratory, Cold Spring Harbor; Peters et al. (1985) Monoklonale Antikörper: Herstellung und Charakterisierung [Monoclonal Antibodies: Preparation and Characterization], Springer Verlag], fused with myeloma cells to generate antibody-producing hybridoma cells, after which suitable clones are isolated and cultured individually. Specific screening methods are used to select the clones which are producing the desired monoclonal antibodies. In this connection, enzyme immunoassay, radio immunoassay and/or Western blotting is/are used to examine the specificity with which the antibodies which are released into the cell culture supernatant bind to, for example, the immunizing antigen or to a possible carrier of the immunizing antigen. Hybridomas which produce antibodies according to the invention are propagated clonally. The hybridoma cell lines which are obtained in this way are then available for producing monoclonal antibodies over an extended period. Relatively large quantities of antibody can be obtained, for example, from cell culture supernatants, in particular from fermentors or roller cultures as well as from ascites.

Depending on the desired purpose, it may be advantageous to use only parts of the antibodies, such as Fab, $F(ab')_2$, or Fab' fragments. The latter can be produced, for example, using the enzymic cleavage methods known to the skilled person [see also Harlow & Lane (1988) Antibodies: A Laboratory Manual, Cold Spring Harbor Laboratory, Cold Spring Harbor].

The antigen-binding sites in an antibody are located in what are termed the variable domains, which are encoded by the V genes. It is also possible to use the known recombinant methods [e.g. Sambrook et al. (1989) Molecular Cloning: A Laboratory Manual, Cold Spring Harbor Laboratory, Cold Spring Harbor, 2nd edition; McCafferty et al. (1990) Nature 348: 552-554] to determine the corresponding nucleic acid sequence of an antibody according to the invention and, as a result, the corresponding amino acid sequence as well, provided the latter had not already been elucidated by means of amino acid sequencing. The hybridoma cells or the antibody-producing immune cells of immunized animals can be used as starting material for these analyses.

Knowing the nucleic acid sequence and/or amino acid sequence, it is then possible to use customary recombinant and molecular biological methods [see also Johnson & Chiswell (1993) Current Opinion in Structural Biology 3: 564-571] to prepare humanized, chimeric, bispecific or oligospecific antibodies, as well as complementarity determining region-derived peptides ("minimal recognition units"), single-chain fragments and/or functional fusion products, e.g. recombinantly prepared antibody-enzyme constructs [see also Larrick & Fry (1991) Human Antibodies and Hybridomas 2: 172-189; Kitano et al. (1986) Appl. Microbiol. Biotechnol. 24:282-286; Thompson et al. (1986) J. Immunol. Methods 94:7-12] which bind to the FSAP MR I-specific epitope, in particular to a peptide according to the invention. These peptides which are encompassed in the term "antibody" can be used, for example, to achieve a decrease in immunogenicity and/or an increase in activity in connection with administration as a pharmaceutical or an in-vivo diagnostic agent, and/or advantages ensue for use of the peptides as or in an in-vitro diagnostic agent. The antibodies can also be prepared, where appropriate with the aid of recombinant methods, in fungi such as yeast cells [Fischer et al. (1999) Biol. Chem. 380: 825-839; Hiatt et al. (1992) Genetic Engineering 14: 49-64], in plant, animal and prokaryotic cells (see also WO 95/25172) as well as in isolated human cells.

This invention furthermore also relates to fungi, animal, plant or prokaryotic cells, as well as isolated human cells, which produce an antibody according to the invention. A preferred embodiment of this invention encompasses hybridoma cell lines which produce the antibodies according to the invention, for example the hybridoma cell lines a) ECE-KLH 2004-9/014, b) ECE-KLH 2004-9/026, c) ECE-KLH 2004-35/05, d) ECE-KLH 2004-34/08, and e) ECE-KLH 2004-151/013, which have been deposited in the DSMZ—Deutsche Sammlung von Mikroorganismen and Zellkulturen [German collection of microorganisms and cell cultures] GmbH, Mascherode Weg 1b, 38124 Braunschweig, Germany, under the receipt numbers a) DSM ACC2675, b) DSM ACC2676, c) DSM ACC2674, d) DSM ACC2725 and e) DSM ACC2726.

The examples which are described below serve to illuminate individual aspects of this invention by way of example and are not to be understood as being a limitation.

EXAMPLES

Example 1

Preparing FSAP Marburg I-Specific Monoclonal Antibodies

1a) Immunizing Mice

BALB/c mice were in each case immunized intraperitoneally with 20 µg of immunizing antigen [KLH-bound peptide having the amino acid sequence Ser-Trp-Gly-Leu-Glu-Cys-Glu-Lys-Arg-Pro-Gly-Val-Tyr (SEQ ID No: 3)] in Immune Easy Mouse adjuvant (Qiagen GmbH, Germany). After 4 and 8 weeks, the mice were given a booster injection with in each case 20 μg of immunizing antigen without adjuvant. For the last 3 days prior to the fusion, the mice were boosted intravenously with in each case 10 μg of immunizing antigen.

1b) Fusion

After the mice had been killed by $CO_2$ inhalation, the spleens were removed and single-cell suspensions were prepared in serum-free Dulbecco's modified Eagle medium (DMEM; PAN Biotech GmbH, Germany). The cells were centrifuged (652×g) and washed 2× in DMEM. The cell count was then determined by means of Trypan Blue staining. $2\times10^7$ myeloma cells (Sp2/0) were added to about $10^8$ spleen cells. Following centrifugation (360×g), the supernatant was discarded and 1 ml of polyethylene glycol solution (PEG 4000, Merck Eurolab GmbH, Germany; approx. 50% strength in DMEM) was added to the cell pellet which, after resuspension, was incubated at 37° C. for 1 minute. Approx. 10 ml of DMEM were then added and the mixture was incubated at room temperature for from 2 to 4 minutes. The fused cells were centrifuged off (326×g) and the pellet was resuspended in DMEM+10% fetal calf serum (Bio Whittaker Europe, Belgium)+HAT medium (CC Pro GmbH, Germany) and aliquoted into 24-well cell culture plates (Corning Costar GmbH, Germany). The approximate cell concentration was $5\times10^4$ to $5\times10^6$ cells per well.

After 2 to 3 weeks, the cell colonies (hybrids) which developed were removed and transferred to new culture plates.

1c) Screening

The specificity of the antibodies which were released into the cell culture was tested in a first test step using microtiter plates (Nunc GmbH & Co. KG, Germany) which were coated with a peptide having the amino acid sequence Ser-Trp-Gly-Leu-Glu-Cys-Glu-Lys-Arg-Pro-Gly-Val-Tyr (SEQ ID No: 3).

100 μl of cell culture supernatant (diluted 1:2) were pipetted into each well of the microtiter plate and the plate was incubated at from +15 to +25° C. for 1 hour. After the plate has been washed twice with POD washing solution (OSEW; Dade Behring Marburg GmbH, Germany), 100 μl of anti-mouse IgG/F(ab')$_2$-POD conjugate (Dade Behring Marburg GmbH, Germany) were aliquoted into each well and the plate was incubated at from +15 to +25° C. for 1 hour. After the plate has been washed a further two times, 100 μl of Chromogen TMB solution (Dade Behring Marburg GmbH, Germany) were aliquoted into each well and the plate was incubated at from +15 to +25° C. for a further 30 minutes. After the incubation, 100 μl of POD stop solution (Dade Behring Marburg GmbH, Germany) were aliquoted into each well and the microtiter plate was evaluated at 450 nm in a BEP II (Behring-ELISA Processor II, Dade Behring Marburg GmbH, Germany).

In a second test step, the hybrids were examined once again in the same test format, as described above, after having been separated into individual cells.

1d) Cloning

Individual cells of hybrids which produce FSAP MR I-specific antibodies were cloned using a micromanipulator (Leitz Messtechnik GmbH, Germany). Culture supernatants from these clones were purified as described under 1g) and characterized in more detail as described under 1e), 1h) and 1i). Antibodies according to the invention which bind to the FSAP MR I-specific epitope are produced, for example, by the clones a) Mab (mouse) directed against ECE-KLH 2004-9/014(1)

b) Mab (mouse) directed against ECE-KLH 2004-9/026 (2), c) Mab (mouse) directed against ECE-KLH 2004-35/05 (1), d) Mab (mouse) directed against ECE-KLH 2004-34/08 (2), and e) Mab (mouse) directed against ECE-KLH 2004-151/013 (2).

These hybridoma cell lines were deposited in the DSMZ-Deutsche Sammlung von Mikroorganismen and Zellkulturen [German collection of microorganisms and cell cultures] GmbH, Mascherode Weg 1b, 38124 Braunschweig, Germany, under the receipt numbers a) DSM ACC2675, b) DSM ACC2676, c) DSM ACC2674, d) DSM ACC2725 and e) DSM ACC2 726.

1e) Determining the Antibody Subclasses

The subclasses of the antibodies directed against the FSAP Marburg I variant were determined using the IsoStrip™ mouse monoclonal antibody isotyping kit supplied by Boehringer Mannheim, Germany. The following subclasses were determined:

a) Mab (mouse) directed against ECE-KLH 2004-9/014 (1)-subclass: IgG 2a, b) Mab (mouse) directed against ECE-KLH 2004-9/026 (2)-subclass: IgG 2a, c) Mab (mouse) directed against ECE-KLH 2004-35/05 (1)-subclass: IgG 2b, d) Mab (mouse) directed against ECE-KLH 2004-34/08 (2)-subclass: IgG 1, e) Mab (mouse) directed against ECE-KLH 2004-151/013 (2)-subclass: IgG 1.

1f) Producing the Antibodies

In order to produce relatively large quantities of antibody, the corresponding cell clones are transferred to roller flasks (Corning Costar GmbH, Germany) and expanded at +37° C. to the desired final volume. After that, the roller culture suspension is filtered through 0.22 μm in order to remove the cells. The antibody solution, which is now cell-free, is concentrated using an ultrafilter (cut-off point 30000 dalton) and then purified.

1g) Purifying the Antibodies

The resulting antibody solution is rebuffered with 0.14 M phosphate buffer, pH 8.6, and loaded onto a chromatography column which is filled with rProtein A Sepharose™ Fast Flow (Amersham Biosciences Europe GmbH, Germany) (1 ml of rProtein A Sepharose™ Fast Flow is used per 10 mg of antibody to be purified). All the unbound components are removed by washing the column with 0.14 M phosphate buffer, pH 8.6. The bound antibody is eluted from the column with 0.1 M citric acid, pH 3.0, and dialyzed against 0.05 M sodium acetate+0.5 M NaCl+0.05 M Tris+0.01% sodium azide, pH 7.0.

1h) Selecting Antibodies which are Suitable for an FSAP Marburg I Sandwich ELISA The reaction of the monoclonal anti-FSAP Marburg I antibodies with the FSAP MR I-specific epitope [peptide having the amino acid sequence Ser-Trp-Gly-Leu-Glu-Cys-Glu-Lys-Arg-Pro-Gly-Val-Tyr (SEQ ID NO: 3)] or the corresponding FSAP wild-type epitope [peptide having the amino acid sequence Ser-Trp-Gly-Leu-Glu-Cys-Gly-Lys-Arg-Pro-Gly-Val-Tyr (SEQ ID NO: 6)] was examined:

Reaction with an FSAP MR I-Specific Peptide:

A microtiter plate which is coated with a peptide having the amino acid sequence Ser-Trp-Gly-Leu-Glu-Cys-Glu-Lys-Arg-Pro-Gly-Val-Tyr (SEQ ID NO: 3) is used as the solid phase. The anti-FSAP MR I antibodies from culture supernatants are incubated on it. After a washing step, a conjugate consisting of rabbit polyclonal anti-mouse antibodies and the enzyme peroxidase is used, together with a subsequent color reaction, to detect binding of the antibody to the peptide.

Reaction with an FSAP Wild-Type Peptide:

A microtiter plate which is coated with a peptide having the amino acid sequence Ser-Trp-Gly-Leu-Glu-Cys-Gly-Lys-Arg-Pro-Gly-Val-Tyr (SEQ ID NO: 6) is used as the solid phase. The anti-FSAP MR I antibodies from culture supernatants are incubated on it. After a washing step, a conjugate consisting of rabbit polyclonal anti-mouse antibodies and the enzyme peroxidase is used, together with a subsequent color reaction, to detect binding of the antibody to the peptide.

Those antibodies which exhibited a reaction with the peptide having the amino acid sequence Ser-Trp-Gly-Leu-Glu-Cys-Glu-LyS-Arg-Pro-Gly-Val-Tyr (SEQ ID NO: 3) (FSAP Marburg I variant) but which, at the same time, did not react with the peptide having the amino acid sequence Ser-Trp-Gly-Leu-Glu-Cys-Gly-Lys-Arg-Pro-Gly-Val-Tyr (SEQ ID NO: 6) (FSAP wildtype) were selected. The suitability of these antibodies for use as solid-phase antibodies in a sandwich ELISA using an FSAP MR I-specific conjugate antibody, which is coupled to horseradish peroxidase employing a method known to the skilled person (e.g. Nakane conjugation), was investigated.

The suitability was examined in a sandwich ELISA as described in Example 3a). The essential criterion for deciding on the suitability was an unambiguous differentiation between the FSAP Marburg I variant and the FSAP wild type, i.e. high signal generation with samples which contain the FSAP Marburg I variant and no, or only a low, signal generation with FSAP wild-type samples. Citrate plasma is the preferred sample type. Other criteria are the lower detection limit and the linearity of the calibration curve.

The antibodies which were produced by the clones a) Mab (mouse) directed against ECE-KLH 2004-9/014(1) (DSM ACC2675), b) Mab (mouse) directed against ECE-KLH 2004-9/026 (2) (DSM ACC2676), c) Mab (mouse) directed against ECE-KLH 2004-35/05 (1) (DSM ACC2674), d) Mab (mouse) directed against ECE-KLH 2004-34/08 (2) (DSM ACC2725) and e) Mab (mouse) directed against ECE-KLH 2004-151/013(2) (DSM ACC2726)

displayed the best results with regard to these criteria.

Example 2

Detecting the FSAP Marburg I Variant in a Sample

2a) Sandwich ELISA Test Method

Peroxidase-conjugated anti-FSAP antibodies were employed, in combination with the monoclonal anti-FSAP Marburg I antibodies according to the invention, in an enzyme immunoassay performed in accordance with the sandwich principle.

During the first incubation, the FSAP Marburg I antigen variant which is present in the sample, provided it is indeed present, binds to the antibodies according to the invention which are directed against FSAP Marburg I and which are fixed to the surface of the wells of a microtitration plate. After the wells have been washed out, peroxidase-conjugated anti-FSAP antibodies which are directed against any arbitrary epitope of the FSAP MR I variant, or of the FSAP wild-type protein, such as those formed by one of the hybridoma cell lines DSM ACC2453 and DSM ACC2454 (EP 1 182 258 A1), are used in a second binding reaction. The excess enzyme-conjugated antibodies are washed out. The enzyme activity which is bound in the wells is then determined. The enzymatic reaction of hydrogen peroxide and tetramethyl-benzidine is terminated by adding dilute sulfuric acid. The color intensity, which is proportional to the FSAP MR I antigen concentration, is determined photometrically at a wavelength of 450 nm and either analyzed qualitatively using a cut-off or quantified using a calibration curve constructed from standards. Such a sandwich immunoassay according to the invention detects the FSAP Marburg I variant specifically in only one test method.

The results are presented in Table 1. The significant color reaction in the samples which are derived from heterozygous test subjects exhibiting FSAP Marburg I polymorphism demonstrates that using the antibodies according to the invention makes it possible to determine the FSAP Marburg I variant specifically and reliably.

2b) LOCI® Test Method

The measurement principle of the LOCI® technology is based on chemiluminescence which is elicited by oxygen free radicals. The prerequisite in this connection is that the reactive components (e.g. chemiluminescence latex particles and photosensitive latex particles) should be in spatial proximity, with this spatial proximity being brought about by the antigen-antibody complex.

A biotin-conjugated anti-FSAP antibody was used, in combination with the monoclonal anti-FSAP Marburg I antibodies according to the invention, in a homogeneous LOCI® performed in accordance with the sandwich principle. During the first incubation, the FSAP Marburg I antigen variant which is present in the plasma sample, if it is indeed present, binds to the antibodies according to the invention which are directed against FSAP Marburg I and which are fixed to the surface of chemiluminescence particles which contain an olefin. After the biotin-conjugated anti-FSAP antibody has been added, and after an incubation of 7 minutes at +37° C., photosensitive latex particles on whose surface streptavidin is fixed are added. If FSAP Marburg I antigen variant is present in the sample, anti-FSAP MR I-chemiluminescence particles, biotin-conjugated anti-FSAP antibodies and photosensitive latex-streptavidin particles then form a spatially close complex. On excitation with light at a wavelength of 680 nm, the photosensitive latex particles release short-lived singlet oxygen, which now initiates a luminescence/fluorescence signal (520-620 nm) from the chemiluminescence particles which are bound by the antigen-antibody complex. As a result of its instability, the singlet oxygen only reaches chemiluminescence particles which are located in the closest vicinity (<200 nm) to the photosensitive latex particles. The emitted light is measured using a modified Tecan RSP 150 having an onboard luminescence detector unit [Ullman et al. (1994), Proc. Natl. Acad. Sci., 91: 5426-5430; Ullman et al. (1996) Clinical Chemistry, 42: 1518-1526].

2c) Detecting the FSAP Marburg I Variant in Patient Samples

The method described under 2a) was used to examine 10 plasma samples, while that described under 2b) was used to examine 84 plasma samples, from test subjects who had previously been genotyped. 5 samples originated from test subjects who had a G/A transition at nucleotide position 1601 of the coding region of the FSAP gene (where 1 is the A of the initiation codon) in one gene copy and were consequently heterozygous carriers of the FSAP MR I polymorphism which, at the amino acid level, leads to a Gly/Glu amino acid substitution at position 534 in the proenzyme (Gly/Glu 534). 5 further samples originated from test subjects who had no mutation at nucleotide position 1601 of the coding region of the FSAP gene but instead exhibited the wild-type gene sequence (G) in both gene copies.

As can be seen from Tables 1 and 2, using an antibody according to the invention in a sandwich ELISA or LOCI® assay makes it possible to differentiate FSAP MR I-positive and FSAP MR I-negative samples unambiguously. The monoclonal antibodies which are formed by the hybridoma cell lines DSM ACC2725 and DSM ACC2726 are particularly suitable for being used in the LOCI® assay. A signal of 300 000 counts was specified as being the cut-off value in the LOCI® assay.

TABLE 1

| Sample No. | Genotype at nucleotide position 1601 | $OD_{450}$ nm |
|---|---|---|
| 10048 | G/G | 0.011 |
| 10032 | G/G | 0.015 |
| 10033 | G/G | 0.016 |
| 10029 | G/G | 0.021 |
| 10045 | G/G | 0.015 |
| 14942 | G/A | 1.625 |
| 14943 | G/A | 1.545 |
| 7020552 | G/A | 1.723 |
| 10047 | G/A | 1.533 |
| 7020538 | G/A | 1.441 |

TABLE 2

| Sample ID | Genotype at nucleotide pos. 1601 | Counts |
|---|---|---|
| 1 | G/G | 8900 |
| 2 | G/A | 1750000 |
| 3 | G/G | 12500 |
| 4 | G/G | 4800 |
| 5 | G/G | 9800 |
| 6 | G/G | 19300 |
| 7 | G/G | 22100 |
| 8 | G/G | 35100 |
| 9 | G/G | 8900 |
| 10 | G/G | 7800 |
| 11 | G/G | 6600 |
| 12 | G/G | 8800 |
| 13 | G/G | 4100 |
| 14 | G/G | 7700 |
| 15 | G/G | 8500 |
| 16 | G/G | 4700 |
| 17 | G/G | 8900 |
| 18 | G/G | 5600 |
| 19 | G/G | 7500 |
| 20 | G/G | 6900 |
| 21 | G/G | 15300 |
| 22 | G/G | 14200 |
| 23 | G/G | 8600 |
| 24 | G/G | 5600 |
| 25 | G/G | 4500 |
| 26 | G/G | 7700 |
| 27 | G/G | 5900 |
| 28 | G/G | 7500 |
| 29 | G/G | 7300 |
| 30 | G/G | 9600 |
| 31 | G/G | 13400 |
| 32 | G/G | 7600 |
| 33 | G/G | 8500 |
| 34 | G/G | 7700 |
| 35 | G/G | 6400 |
| 36 | G/G | 5600 |
| 37 | G/G | 7600 |
| 38 | G/G | 9100 |
| 39 | G/G | 7300 |
| 40 | G/G | 9800 |
| 41 | G/G | 4900 |
| 42 | G/G | 8500 |
| 43 | G/G | 25400 |
| 44 | G/G | 12400 |
| 45 | G/G | 31200 |
| 46 | G/G | 22200 |
| 47 | G/G | 8600 |
| 48 | G/A | 1821000 |
| 49 | G/G | 5300 |
| 50 | G/G | 7600 |
| 51 | G/G | 9400 |
| 52 | G/G | 5900 |
| 53 | G/G | 7800 |
| 54 | G/G | 8800 |
| 55 | G/G | 24500 |
| 56 | G/G | 21500 |
| 57 | G/G | 27400 |
| 58 | G/G | 23300 |
| 59 | G/G | 14600 |
| 60 | G/G | 7300 |
| 61 | G/G | 5600 |
| 62 | G/G | 9600 |
| 63 | G/G | 6700 |
| 64 | G/G | 21400 |
| 65 | G/A | 1250000 |
| 66 | G/G | 8300 |
| 67 | G/G | 7900 |
| 68 | G/G | 6900 |
| 69 | G/G | 4900 |
| 70 | G/G | 8800 |
| 71 | G/G | 15400 |
| 72 | G/G | 18800 |
| 73 | G/G | 7700 |
| 74 | G/G | 8300 |
| 75 | G/G | 5700 |
| 76 | G/A | 1479000 |
| 77 | G/G | 7800 |
| 78 | G/G | 8800 |
| 79 | G/G | 9400 |
| 80 | G/G | 5800 |
| 81 | G/G | 6400 |
| 82 | G/G | 7600 |
| 83 | G/G | 8200 |
| 84 | G/G | 6900 |

The invention claimed is:

1. An antibody produced by a hybridoma cell line chosen from DSM ACC2674, DSM ACC2675, DSM ACC2676, DSM ACC2725, and DSM ACC2726.

2. The antibody of claim 1, wherein the antibody is linked to at least one of a solid phase and a component of a signal-generating system.

3. A cell line which produces the antibody of claim 1, comprised of isolated cells chosen from animal, plant, fungal, and prokaryotic cells.

4. The cell line of claim 3, wherein the isolated cells are hybridoma cells.

5. The cell line of claim 4, chosen from DSM ACC2674, DSM ACC2675, DSM ACC2676, DSM ACC2725, and DSM ACC2726.

6. A method of separating molecules comprising the amino acid sequence of SEQ ID NO:1 from other molecules, comprising:
    linking at least one antibody of claim 1 to a solid phase;
    contacting the solid phase with a sample that may comprise at least one molecule comprising the amino acid sequence of SEQ ID NO:1;
    washing the solid phase; and
    eluting the at least one molecule comprising the amino acid sequence of SEQ ID NO:1 from the solid phase.

7. A method of detecting at least one FSAP Marburg I variant in a sample, comprising:
    providing a sample which may comprise at least one FSAP Marburg I variant antigen;
    contacting the sample with at least one antibody of claim 1, wherein the antibody is linked to a signal generating system comprising a label; and
    detecting a signal from the specific binding of the antibody to the at least one FSAP Marburg I variant antigen with the label, thereby detecting an FSAP Marburg I variant antigen in the sample.

8. The method of claim 7, wherein the at least one FSAP Marburg I variant comprises the amino acid sequence of SEQ ID NO:3.

9. The method of claim 7, wherein the antibody is linked to a solid phase.

10. The method of claim 7, wherein the signal from the label is quantitated.

* * * * *

UNITED STATES PATENT AND TRADEMARK OFFICE
CERTIFICATE OF CORRECTION

| | | |
|---|---|---|
| PATENT NO. | : 7,622,558 B2 | Page 1 of 1 |
| APPLICATION NO. | : 11/208881 | |
| DATED | : November 24, 2009 | |
| INVENTOR(S) | : Schwarz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 178 days.

Signed and Sealed this

Twenty-sixth Day of October, 2010

David J. Kappos
*Director of the United States Patent and Trademark Office*